(12) United States Patent
Ghosh et al.

(10) Patent No.: US 10,520,435 B2
(45) Date of Patent: Dec. 31, 2019

(54) OPTICAL SENSOR AND SENSING SYSTEM FOR OXYGEN MONITORING IN FLUIDS USING MOLYBDENUM CLUSTER PHOSPHORESCENCE

(75) Inventors: Ruby N. Ghosh, Okemos, MI (US); Reza Loloee, Lansing, MI (US); Per A. Askeland, East Lansing, MI (US); Christopher T. Weeks, Lansing, MI (US)

(73) Assignee: OptiO2, LLC, Okemos, MI (US)

( * ) Notice: Subject to any disclaimer, the term of this patent is extended or adjusted under 35 U.S.C. 154(b) by 496 days.

(21) Appl. No.: 13/883,759

(22) PCT Filed: Nov. 4, 2011

(86) PCT No.: PCT/US2011/059361
§ 371 (c)(1),
(2), (4) Date: May 6, 2013

(87) PCT Pub. No.: WO2012/061724
PCT Pub. Date: May 10, 2012

(65) Prior Publication Data
US 2014/0017127 A1    Jan. 16, 2014

Related U.S. Application Data

(60) Provisional application No. 61/410,254, filed on Nov. 4, 2010.

(51) Int. Cl.
*G01N 21/64*    (2006.01)
*G01N 21/77*    (2006.01)

(52) U.S. Cl.
CPC ....... *G01N 21/643* (2013.01); *G01N 21/6428* (2013.01); *G01N 2021/772* (2013.01); *Y10T 436/209163* (2015.01)

(58) Field of Classification Search
None
See application file for complete search history.

(56) References Cited

U.S. PATENT DOCUMENTS

| | | | | |
|---|---|---|---|---|
| 5,173,432 A | * | 12/1992 | Lefkowitz et al. | 436/138 |
| 5,656,241 A | * | 8/1997 | Seifert et al. | 422/82.06 |
| 6,328,932 B1 | * | 12/2001 | Carter et al. | 422/82.06 |
| 2002/0098120 A1 | * | 7/2002 | Blazewicz et al. | 422/82.07 |
| 2006/0199088 A1 | * | 9/2006 | McCollough et al. | 430/30 |

OTHER PUBLICATIONS

Ghosh, Fiber-optic oxygen sensor using molybdenum chloride cluster luminescece, Applied Physics Letter, vol. 75, No. 19, pp. 2885-2887, Nov. 8 1999.*

* cited by examiner

*Primary Examiner* — Neil N Turk
(74) *Attorney, Agent, or Firm* — Scherrer Patent & Trademark Law, P.C.; Stephen T. Scherrer; Monique A. Morneault

(57) ABSTRACT

A composite comprises a polymer matrix and a luminophore dispersed therein. The composite is useful as a sensing film that is used as an optical sensor for oxygen measurement comprising the composite sensing film; a source of photons for photo-exciting the luminophores and a waveguide, transparent in the frequency range of the excitation photons, for guiding the excitation photons from the source to the composite sensing film; a detector for measuring properties of photons emitted from the luminophores. A system including a computer may be useful for coordinating the activities of the sensor.

42 Claims, 6 Drawing Sheets

OPTICAL SENSOR AND SENSING SYSTEM FOR OXYGEN MONITORING IN FLUIDS USING MOLYBDENUM CLUSTER PHOSPHORESCENCE

CROSS-REFERENCE TO RELATED APPLICATIONS

This application claims the benefit of U.S. Provisional Application No. 61/410,254, filed Nov. 4, 2010 which is incorporated herein by reference in its entirety.

BACKGROUND

The present invention discloses an optical sensor for detecting and/or quantifying oxygen based on a luminophore dispersed in a polymer matrix and methods for using said sensor, often for the purpose of monitoring chemical and biological processes.

Oxygen sensors for fluids fall into two general categories, electrochemical sensors and optical sensors.

Electrochemical sensors typically employ an electrode that is placed in a fluid in which oxygen is to be measured. The basic principal is that the electrode has both a cathode and an anode. Oxygen enters the electrode, typically through a permeable membrane, and is reduced at the cathode, creating a measurable electric current. Note that an electrochemical sensor measures an ionic current, the specificity to oxygen is determined solely by the ability of the permeable membrane to exclude unwanted species. The current produced is proportional to the oxygen concentration. While these sensors are considered the "gold" standard for measuring oxygen due to the long history of use, they suffer from significant limitations; including consuming oxygen (the analyte being monitored), requiring a flowing fluid, being sensitive to environmental factors, and drifting over time (due to electrolyte consumption).

Optical sensors typically use luminescent molecules embedded in a sensing film that is placed in the fluid in which oxygen is to be measured. The luminescent molecules are photoexcited and either the lifetime or intensity of the emitted luminescence is measured. Due to changes in the luminescence caused by the presence of oxygen, said measurement is indicative of oxygen concentration. Current optical oxygen sensors suffer from degradation, called "photobleaching," which limits the total number of measurements possible with a single sensor, forcing the choice between frequent measurements over a short period or a sparse data set over a long period, as shown, for example, in Draaijer U.S. Pat. No. 7,695,679 for the Ru complexes and S. M Borisov, G. Nuss 7 I. Kimant, Anal. Chem 80 9435 (2008) for the Pt and Pd porphyrines. Current optical oxygen sensors cannot simultaneously satisfy the requirements of (i) sensitivity, (ii) specificity to oxygen, i.e. lack of cross sensitivity to other species in the fluid, (iii) continuous monitoring without restrictions on the data collection protocol, and (iv) minimal coupling to changes in the environment.

Real-time detection of oxygen in fluids is important for a variety of chemical and biological processes ranging from aquaculture to industrial process control. For example, dissolved oxygen is considered a principal limiting factor in aquaculture production systems. Bio-reactors and the food/beverage industry require real-time monitoring of oxygen for process control. Water quality and environmental applications such as EPA remediation sites, monitoring the impact of oil spills on marine biology, and mining require continuous (24/7) remote oxygen monitoring. Bio-medical applications such as in-vitro studies of the anaerobic growth of cancer cells and in-vivo measurements of dissolved oxygen in organs or tissue require oxygen sensors that are not affected by constituents of the fluid under study. However, current oxygen sensors do not possess the capabilities needed for such applications.

An oxygen sensor for such applications preferably possesses a number of key attributes. First, such a sensor is preferably unaffected by environmental factors such as salinity, pH, phosphates, $CO_2$, and biological waste, all with a minimum temperature dependence. Second, such a sensor preferably provides for real-time continuous monitoring of oxygen without limitations on the number of data points. Third, such a sensor preferably exhibits no photobleaching, a long luminescence lifetime, a large Stokes shift and high quantum efficiency. Fourth, the sensor preferably is capable of monitoring physically remote locations and may preferably be miniaturized into a small flexible probe.

Improvements in sensor technologies are always sought in order to improve the various chemical and biological processes, such as those identified above, which rely on sensors. An oxygen sensor with the attributes identified above would represent a significant advance in the field.

SUMMARY

The present invention discloses an optical sensor for oxygen measurement comprising a composite sensing film containing luminophores dispersed in a polymer matrix; a source of photons for photoexciting the luminophores and a waveguide, transparent in the frequency range of the excitation photons, for guiding the excitation photons from the source to the composite sensing film; a detector for measuring properties of photons emitted from the luminophores and a waveguide, transparent in the frequency range of the emitted photons, for guiding the emitted photons from the composite sensing film to the detector; and a system for coordinating the activities of the sensor.

In one embodiment, the sensor may be configured as a reflection-mode sensor. In said configuration, the sensing film is located at the distal end of the waveguide, and the source and the detector are located at the proximal end of the waveguide. In certain embodiments, the waveguides may be combined into a single waveguide and may be constructed from one or more optical fibers. Advantages of the reflection mode configuration include (i) the sensing film can be located in a harsh environment (bottom of a well or catheterized inside an animal), far (km if necessary) from the source and detector; (ii) optical fibers are rugged yet extremely flexible allowing for miniaturized flexible probes; and (iii) immunity from electrical interference (unlike any electrochemical sensor).

The polymer matrix is preferably any oxygen permeable, optically transparent, hydrophobic polymer or co-polymer matrix. In one embodiment of the present invention, the polymer matrix is photo-cured silicone. The luminophore is any photoexcitable molecular substance that following excitation emits a luminescence. For use as an oxygen sensor, the luminescence must be changed in some manner due to the presence of oxygen, thus the luminescence is correlated to the oxygen concentration in the fluid. In one embodiment of the present invention, the luminophore is a molybdenum cluster, the luminescence of which is quenched by oxygen. In certain embodiments, the salts of the molybdenum clusters are preferred due to their optical and thermal stability. Without being bound by theory, isolated monomers of the molybdenum cluster immobilized in the matrix are preferred as they maintain the long phosphorescence lifetime and high quantum efficiency of the luminophore. Typically, prior art oxygen sensors utilizing luminophores within a carrier material, such as polymer or a ceramic, for example, exhibit significant photobleaching during use. Photobleaching, generally, is the loss of sensitivity of the oxygen sensor caused by the photodestruction of the luminophore as the oxygen sensor is used. Indeed, many prior art oxygen sensors are unusable after a certain number of measurements due to this condition. In embodiments of the present invention, as described herein, photobleaching is substantially reduced, if not eliminated, over a testing period, which is a surprising result.

In a particularly preferred embodiment, the sensing film is a composite comprising a suitable polymer which contains isolated monomers of the luminophore, the composite having the following properties: (i) oxygen permeability, (ii) optical transparency, (iii) chemical inertness, and (iv) mechanical robustness. In certain applications, specifically those in which the luminescence of the luminophore is disrupted by contact with water and/or water vapor and/or other water-borne constituents in the fluid being measured, the composite is also preferably hydrophobic. The embodiments described herein are substantially, if not completely, free of photobleaching. In the particularly preferred embodiment, all properties listed above are present in the composite sensing film of the present invention.

In a preferred embodiment, use of a sensing film comprising molybdenum chloride clusters and made from photocurable silicone polymers leads to a sensor that is robust (reversible and high signal/noise ratio), substantially, if not completely, free of photobleaching, and advantageously unaffected by environmental conditions such as pH, salinity, $CO_2$ and the like. The sensing film has an acceptably small temperature dependence which can be easily accommodated.

Optionally, the composite sensing film may either be placed on top of a transparent substrate or may be self-standing. Optionally, the composite sensing film may be provided with a light blocking coating on the side opposite to that used to couple in and out the excitation and emission signals. Optionally, the waveguide for guiding the excitation photons and the waveguide for guiding the emitted photons may be combined into a single waveguide.

The present invention further discloses a process for using a sensor to quantify the output from the detector by measuring the intensity, lifetime, or phase angle rotation of the emitted luminescence from the composite sensing film wherein the intensity, lifetime, or phase angle rotation is correlated to the oxygen level in the fluid by the relationship described in the Stern-Volmer equation.

The present invention further discloses the use of software, running on one or more computers, as the system for coordinating activities of the sensor. The software may additionally be used to bias the quantified sensor output, for example, due to ambient temperature. The software may also use the quantified output from the detector to control a process, such as adjusting a process parameter or notifying a human operator that the quantified value has deviated beyond some predetermined bounds.

Further, there is a composition suitable for use in forming the composite sensing films. The composition can be provided in a kit form, optionally together with an initiator composition and instructions to make sensor films as further described herein. The composition comprises a polymer and a molybdenum cluster, wherein the polymer is selected from the group consisting of a photocurable silicone and a methacrylate polymer, and the molybdenum cluster comprises a hexanuclear molybdenum compound selected from the group consisting of those of formula (1) and those of formula (2), as further described below.

These features of the present invention are useful in improving a variety of industrial processes, as the present invention addresses each of the needs identified previously.

BRIEF DESCRIPTION OF THE DRAWINGS

The drawings described herein are for illustrative purposes only of selected embodiments and not all possible implementations, and are not intended to limit the scope of the present disclosure. Note that the dimensions are not necessarily to scale.

DEFINITIONS

Figure 1:
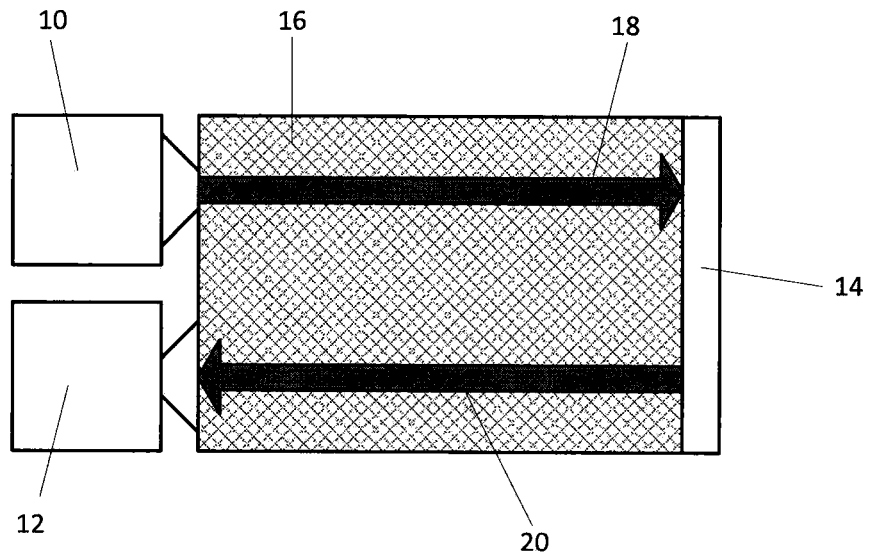
FIG. 1 is a schematic representation of a reflection mode sensor.

The following definitions apply to certain terms used in the specification:

Aqueous: Any fluid in which one component is water.

Emission lifetime ($\tau$): Following absorption of excitation photons, the longest exponential decay constant of the emitted luminescence is defined as the emission lifetime. $\tau_0$ is the unquenched emission lifetime of a luminophore in an oxygen free environment. $\tau_0$ (solution) is the unquenched emission lifetime of a luminophore in a preferred solution, wherein the preferred solution is a solution of one or more solvents in which the optical luminescence of the luminophore versus concentration of luminophore in the solution is linear. $\tau_0$ (composite) is the unquenched emission lifetime of a composite of the present invention in a fluid of interest. $\tau_{21}$ is the quenched emission lifetime of a luminophore in the presence of 21% oxygen and the balance nitrogen gas. $\tau_{21}$ (solution) is the quenched emission lifetime of a luminophore in a preferred solution, wherein the preferred solution is a solution of one or more solvents in which the optical luminescence of the luminophore versus concentration of luminophore in the solution is linear. $\tau_{21}$ (composite) is the quenched emission lifetime of a composite of the present invention in a fluid of interest.

Fluid: Any environment comprising any mixture of liquids and/or gases in any proportion.

Luminophore: An atom or atomic grouping in a chemical compound that manifests luminescence. Although the present invention generally refers to and describes an exemplary luminophore, "molybdenum cluster", as defined below, it should be noted that any luminophore may be utilized having the properties described herein when formed into a composite, and the invention should not be limited as described herein.

Luminescence: Either fluorescence or phosphorescence emitted by a luminophore. Depending on the spin state of the electronic level, the emitted luminescence is defined as fluorescence when both excited and ground state have the same spin multiplicity, or as phosphorescence when the excited and ground states have different spin multiplicity.

Molybdenum cluster: A luminophore comprising a hexanuclear molybdenum compound of the formulas:

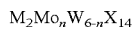

where M is a cation selected from Na$^+$, K$^+$, and NH$_4^+$, each X is independently a monoanionic ligand, for example a halide selected from Cl$^-$, Br$^-$, F$^-$, I$^-$ and At$^-$, and n is from 0 to 6; or

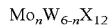

where n is from 0 to 6, and each X is independently a monoanionic ligand, as disclosed above.

The hexanuclear molybdenum cluster is a preferred luminophore for detecting triplet oxygen as the excited state of the cluster is a spin triplet, whereas the ground state is a spin singlet, therefore the emitted luminescence is phosphorescence with a long lifetime. An additional advantage of this luminophore is the large quantum efficiency (number of photons emitted per excitation photon) Another additional advantage is the specificity of this luminophore for detecting oxygen is governed by quantum mechanics as the phosphorescence is uniquely quenched by a molecule with spin triplet ground state symmetry, i.e. $^3O_2$.

Oxygen: A molecule composed of two oxygen atoms. The molecule can exist in one of two states; the ground state with a spin quantum number of 3 (called triplet) or the excited state with a spin quantum number of 1 (called singlet).

Photobleach: A process by which the luminescent properties of the luminophore are degraded or destroyed following repeated photoexcitation.

Photoexcitation: The mechanism of electron excitation by photon absorption, when the energy of the photon is too low to cause photoionization. The absorption of photons takes place in accordance to the Planck's Quantum Theory.

Quenching Ratio (Q): $\tau_0$ (composite)/$\tau_{21}$ (composite)

UV: Electromagnetic radiation with a wavelength shorter than that of visible light, but longer than X-rays. In the context of this disclosure, UV is used generically to mean a portion of the spectrum which ranges from the wavelength of the excitation photons to the wavelength of the luminesced photons in a reflection mode sensor.

Waveguide: A device for guiding photons from one location to another. A waveguide may comprise one or more individual elements, acting in concert. An exemplary waveguide comprises a fiber optic cable or bundle.

DESCRIPTION

The following description is merely exemplary in nature and is not intended to limit the present disclosure, application, or uses. It should also be understood that throughout the reference numerals indicate like or corresponding parts and features. In respect of the methods disclosed, the order of the steps presented is exemplary in nature, and thus, is not necessary or critical, unless otherwise noted. In addition, while much of the present invention is illustrated using specific examples, the present invention is not limited to these embodiments. All publications, patent applications, patents, and other references mentioned herein are incorporated by reference in their entireties. In case of conflict, the present specification, including definitions, will control.

FIG. 1 provides a schematic of a reflection mode sensor. The sensor comprises four basic components: a source of excitation photons 10, a detector for luminesced photons 12, a sensing film 14, and an optical waveguide 16. The sensing film 14 contains luminophores, which upon being excited by photons 18 from source 10 emit photons 20, with a different wavelength, which are detected by detector 12. The waveguide 16 is optically transparent at both the wavelength of the excitation photons 18 and the luminesced photons 20.

The waveguide need not be a monolithic waveguide as depicted in FIG. 1. It may comprise a plurality of optical waveguides, with some number of which used to transmit the excitation photons 18 to the sensing film 14 and which are transparent at the wavelength of the of the excitation photons 18; with the remaining number of which used to transmit the luminesced photons 20 to the detector and which are transparent at the wavelength of the luminesced photons 20. In an exemplary embodiment, the waveguide comprises an optical fiber or an optical fiber bundle capable of transmitting exciting light 18, in the 330-400 nm range, and transmitting back to the detector the emitted light 20, in the range of 600-900 nm.

Figure 2:
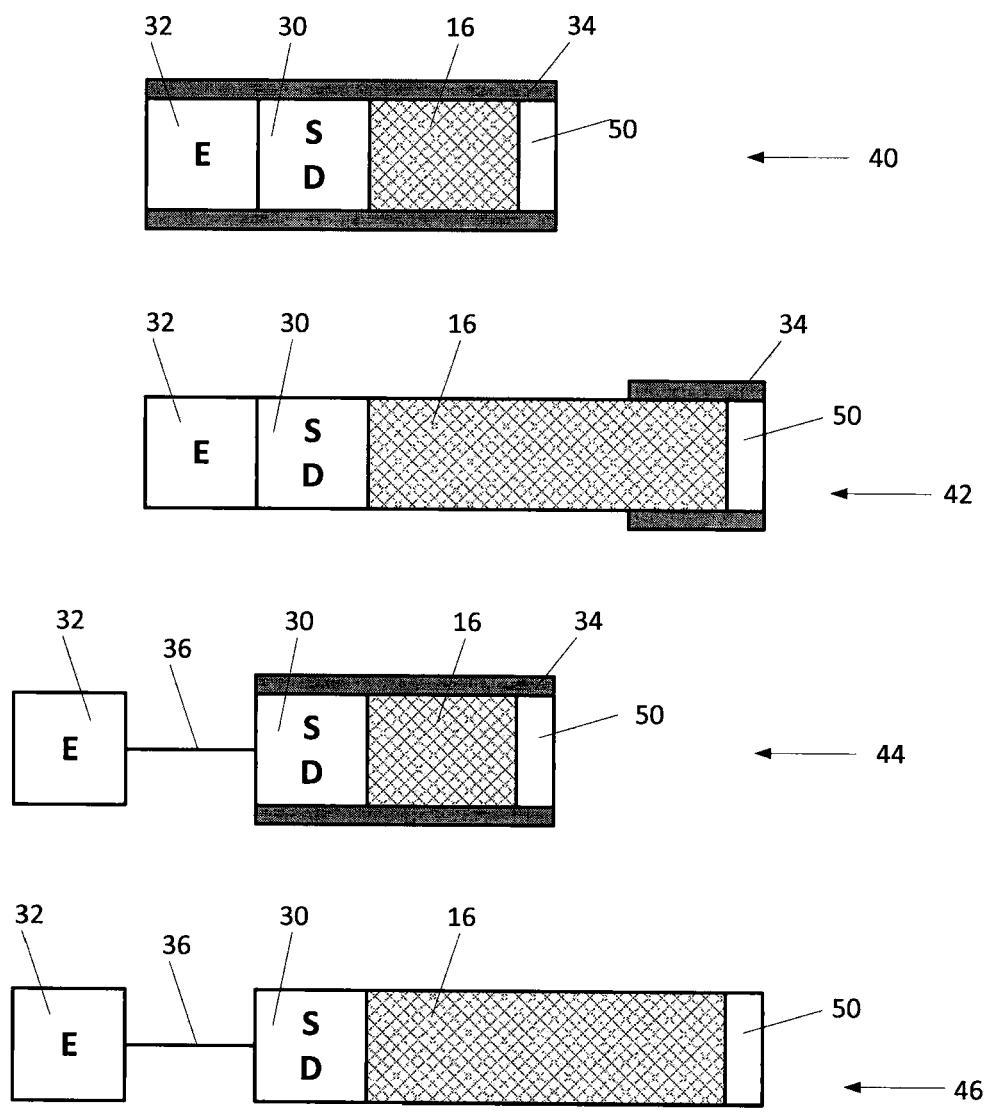
FIG. 2 shows a depiction of several of the possible configurations for a reflection mode sensor.

FIG. 2 depicts several of the possible configurations for a reflection mode sensor from the perspective of the physical relationship between the components of the sensor. The components shown are a sensing film assembly 50; the optical waveguide 16; a sensing/detecting module 30, which contains both the source of excitation photons 10 and the detector for luminesced photons 12; an electronics module 32, which coordinates the activities of the sensing/detecting module 30, optionally quantifies the output of detector 12, and optionally converts the quantified output into a digital signal, e.g., a serialized bit stream; and an optional encasement 34 for isolating enclosed components from an external environment. To use the reflection mode sensor, one major surface of the sensing film assembly 50 must be in contact with, or be immersed in, the fluid in which oxygen is to be measured.

Configuration 40 depicts a monolithic reflection mode sensor in which all components are located within the encasement 34 and which provides a digital output signal. This configuration yields a compact sensor which can be located remotely from a control center as the digital output can be transported any distance without loss.

Configuration 42 depicts a reflection mode sensor in which the sensing component is located within the encasement 34; the sensing/detecting module 30 and electronics module 32 are located remotely from the sensing film assembly 50; and which provides a digital output signal. This configuration provides the ability to have a very small portion of the sensor be placed in a challenging environment while having the larger, possibly environmentally sensitive components, be located elsewhere. Since the signal from the sensing film assembly 50 to the sensing/detecting module 30 is transmitted optically, separations of thousands of meters are possible. If longer separations are needed, an optical amplifier could be installed.

Configuration 44 depicts a reflection mode sensor in which the electronics module 32 is physically separated from the remainder of the sensor. In this configuration, a wire 36 is used to transmit electrical signals between the electronics module 32 and the sensing/detecting module 30. This configuration is advantageous because many existing sensors are configured in this manner, thus the present invention could be used as a drop-in replacement for existing sensors.

Configuration 46 depicts a reflection mode sensor in which the sensing film assembly 50 is directly attached to the waveguide 16 and the electronics module 32 is physically separated from the remainder of the sensor. In this configuration, a wire 36 is used to transmit electrical signals between the electronics module 32 and the sensing/detecting module 30. This configuration is advantageous because it provides a means to maximally reduce the size of the probe to connect the sensor to standard laboratory-type equipment.

The sensing/detecting module 30 and the electronics module 32 are sized to meet the specific application requirements of the sensor. For the configuration 40, it may be desirable for these modules to be custom-designed and very compact in size in order to minimize the size of the encasement 34. For the configuration 42, these modules may be off-the-shelf laboratory units capable of providing the necessary functionality.

It should be apparent to those skilled in the art that there are numerous mechanical configurations which may satisfy the different sensor configurations and which may further add utility by facilitating sensor construction and/or maintenance. For a first example, after the sensing film assembly 50 is prepared, it may be inserted into a screw-on cap. This screw-on cap may then be attached to the encasement 34, optionally providing a hermetic seal to protect the proximal surface of the sensing film 14 from the fluid under test. For a second example, the sensing film assembly 50, the waveguide 16, and the sensing/detecting module 30 may all be inserted into the encasement 34 and then affixed into place using an adhesive. It should also be appreciated that the physical size and shape of the encasement 34 may be such that it allows for the present invention to be used as a direct replacement for standard electrochemical dissolved oxygen probes.

Figure 3:
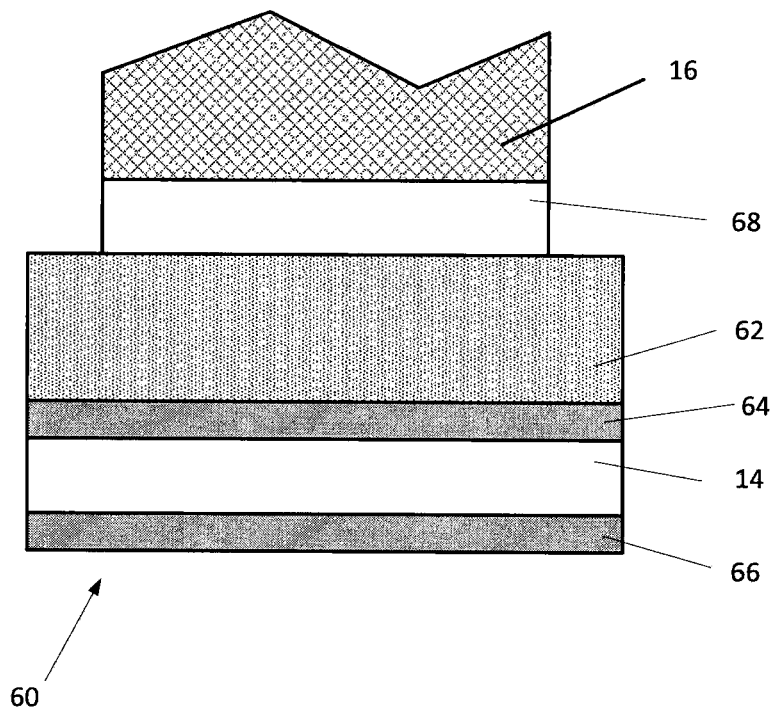
FIG. 3 is a schematic drawing of a sensing film assembly which employs a substrate located between the sensing film and the waveguide.

FIG. 3 provides a schematic of an embodiment of a sensing film assembly 60 and for optically connecting the sensing film assembly 60 to a waveguide 16. In this embodiment, a substrate 62 is located between the sensing film and the waveguide. In the description for FIGS. 3 and 4, when referring to a major surface of an element, the term 'proximal' shall mean that major surface which is closer, in the sense of an optical path, to the sensing/detecting module 30; and 'distal' shall mean that major surface which is farther, in the sense of an optical path, from the sensing/detecting module 30.

The embodiment of the sensing film assembly 60 comprises the substrate 62, a primer 64, the sensing film 14, and a light blocking film 66. The sensing film assembly 60 is connected to the waveguide 16 with the aid of an optional index matching material 68. As shown, the waveguide 16 is in contact with (or is optically coupled to) the proximal surface of the substrate 62. The distal surface of the substrate 62 is in contact with the proximal surface of the optional primer 64. The distal surface of the primer 64 is in contact with the proximal surface of the sensing film 14. The distal surface of the sensing film 14 is in contact with the proximal surface of the optional blocking film 66. Though depicted as a separate layer, in certain embodiments, the light blocking functionality of the light blocking layer 66 may be directly incorporated into the distal surface of the sensing film 14. The distal surface of the blocking film 66 is the part of the sensor that is in contact with the fluid to be monitored or measured. As such, it forms the "outside" layer of the sensor or sensor assembly.

In certain embodiments of the sensing film assembly 60, the widths of the components may differ. An en exemplary example, the sensing film 14 may be fabricated in such a manner that it is completed enveloped by the substrate 62 and/or the light blocking layer 66. There are other variations of this construct which are obvious to those skilled in the art.

Figure 4:
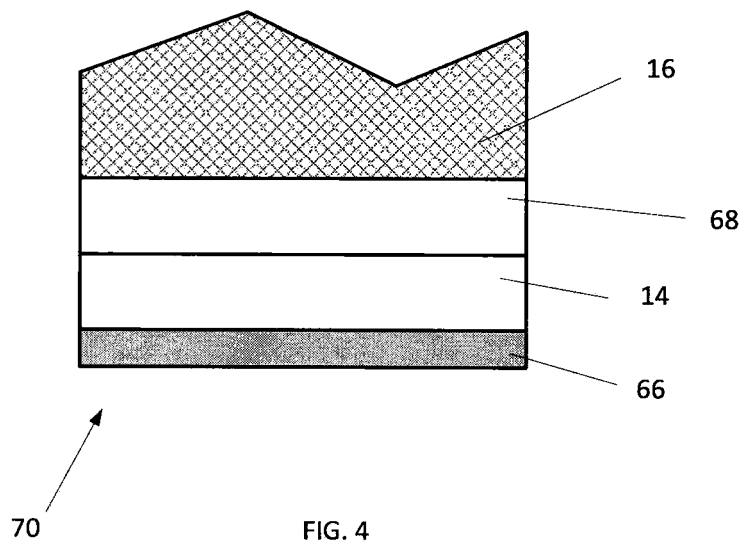
FIG. 4 is a schematic drawing of a sensing film assembly which does not employ a substrate.

FIG. 4 provides a schematic of an embodiment of a sensing film assembly 70 which does not employ a substrate and for optically connecting the sensing film assembly 70 to a waveguide 16.

The embodiment of the stand-alone sensing film assembly 70 comprises the sensing film 14 and a light blocking film 66. The sensing film assembly 70 is connected to the waveguide 16 with the aid of an optional index matching material 68. As shown, the waveguide 16 is in contact with (or is optically coupled to) the proximal surface of the sensing film 14. The distal surface of the sensing film 14 is in contact with the proximal surface of the optional blocking film 66. Though depicted as a separate layer, in certain embodiments, the light blocking functionality of the light blocking layer 66 may be directly incorporated into the distal surface of the sensing film 14. The distal surface of the blocking film 66 is the part of the sensor that is in contact with the fluid to be monitored or measured. As such, it forms the "outside" layer of the sensor or sensor assembly.

The following paragraphs disclose further information about key components of the oxygen sensor system.

Index Matching Material

An index matching material is used to provide a continuous optical path of constant refractive index. For the sensing film assembly 60, the index matching material 68 may be placed between the waveguide and the sensing film 14. The index matching material 68, often in the form of a gel, provides one way of optically coupling the fiber to the sensor assembly. A non-limiting example is the clear, optical coupling gel, Nyogel OC-431A, (with n=1.456@$\lambda$=632.8 nm) available from Nye Lubricants, Inc. 12 Howland Road, Fairhaven, Mass. 02719 U.S.A.

Substrate

A substrate is used to provide support for a sensing film. Suitable substrates 62 are those which provide necessary support for the sensing film 14 and which are transparent in the wavelengths of the of the excitation photons 18 and the luminesced photons 20, which in certain embodiments may be ultraviolet. There are two basic classes of substrate materials—those which are rigid and those which are non-rigid.

Non-limiting examples of rigid substrate materials include quartz, a technical name for glass with low enough impurities to be UV transparent; and a UV transparent optical fiber. In certain embodiments, one side of the substrate may be frosted with the sensing film being applied to the frosted side, for example a frosted glass slide. It is believed that the frosting promotes adhesion of the sensing film because of the increased surface area on the frosted side of a glass substrate. The frosting is additionally believed to improve sensor performance by preferentially scattering the excitation photons throughout the sensing film, thereby increasing the luminescence; and by preferentially scattering the emitted photons back to the detector, thereby increasing the detector signal.

A non-limiting example of a non-rigid substrate material is poly-methyl-methacrylate (PMMA) that is specifically formulated to be UV transparent. In certain embodiments, the substrate 62 may be UV transparent silicone which is formed around the sensing film 14. This approach, combined with encasement with a screw-on cap, provides an easy, low-cost approach to replacing a sensing film, for example, should the sensing film be damaged during operation.

Primer

Primers are used to match the properties of two materials, typically to promote their adhering to each other. In certain embodiments, the sensing film 14 is non-polar with relatively high coefficient of thermal expansion. Depending on the substrate 62, these properties can create problems with adhesion due to lack of matching of the properties. For example, quartz has both a polar surface and a relatively low coefficient of thermal expansion. As a result, there is a possibility that even slight temperature variations could lead to thermally induced stress at the interface between the sensing film 14 and the substrate 62, which could result in spontaneous delamination.

Where necessary to avoid such problems, the primer 64 can be disposed between the substrate and the sensing film to act as an adhesion promoter. As an exemplary example, for a sensing film assembly 60 comprising a quartz substrate 62 and a acrylate- or methacrylate-functional polydimethylsiloxane based sensing film 14, methacryloxymethyltrioxysilane may be used as a primer material. It adheres to the quartz substrate 62 by silane-silica interaction and to the sensing film 14 by a crosslinking through the methacrylate functional group Sensing Film The sensing film is generally formed by immobilizing the luminophore in a well dispersed manner throughout the matrix. In an exemplary embodiment, and without being bound by theory, the sensing film is a composite formed by immobilizing isolated monomers of the luminophore in a well-dispersed manner throughout the matrix. For purposes of the present invention, a composite having isolated monomers of the luminophore well-dispersed throughout the matrix is shown if:

$\tau_0$ (solution)/$\tau_0$ (composite)≤3.5; and

Q≥2.5.

The synthetic route, as described herein, allows "caging" of the molybdenum clusters in a well-dispersed manner during densification or polymerization of the support matrix without degradation of the optical properties of the molybdenum cluster. The composite (molybdenum cluster/polymer matrix) sensing film is preferably (i) oxygen permeable, (ii) optically transparent, (iii) chemically impervious to any constituents (beside oxygen) in the fluid, and (iv) mechanically robust. It is particularly preferred that the sensing film simultaneously contain these properties. In certain applications, specifically those in which the luminescence of the luminophore is disrupted by contact with water and/or water vapor and/or other water-borne constituents in the fluid being measured, the composite is preferably hydrophobic.

Oxygen permeability is generally necessary for a reversible, non-hysteretic sensor with a fast response time. For purposes of the present invention, the sensing film, in a preferred embodiment, has sufficient oxygen permeability when the response time of the composite film in the fluid under the test has the following values for $t_{90}$:

(i) 21% oxygen (synthetic air) to 0% oxygen, $t_{90}$≤30 s; and
(ii) 0% oxygen to 21% oxygen (synthetic air), $t_{90}$≤20 s where $t_{90}$ is defined as the time needed to reach 90% of the steady state value, and 0% oxygen is defined as 99.999% pure nitrogen gas. The response time test is to be performed at 22° C. by exchanging the composite film between two vessels in which the fluid has come to equilibrium with 0% oxygen and 21% oxygen respectively.

Optical transparency is generally necessary for efficient propagation of the excitation photons into the sensing film and the luminesced photons out of the film (i.e., a sensor with high signal/noise ratio). Optical transparency, for purposes of the present invention, is defined as the ratio of the intensity of light exiting the composite film divided by the intensity of light incident on the composite film, measured at both the excitation wavelength and the emission wavelength of the composite film. For purposes of the present invention, the sensing film, in a preferred embodiment, has sufficient optical transparency when the transparency of the sensing film is ≥99.0%.

Another particularly preferred property includes being chemically impervious to other constituents or interferents that may be present in the tested fluid for ensuring that the sensing film does not degrade so that it properly luminesces thereby rendering the detection of oxygen robust and accurate. Common interferents may include salt (i.e., sodium chloride in the concentration of sea water), gaseous $CO_2$, acids and bases causing pH in the range of about 2 to about 12, alcohols such as methanol and ethanol, glucose, ammonium, common solvents such as isopropanol, and common buffers used in bioreactors. For purposes of the present invention, the sensing film, in a preferred embodiment of the present invention, is chemically impervious to other constituents (besides oxygen) in the tested fluid when, following one day of exposure in the fluid tested, the change of the quenching ratio will be ≤5%.

In addition, a further particularly preferred property of the present invention includes being mechanically robust so that the sensor works accurately over relatively long periods of time to detect oxygen in a tested fluid. For purposes of the present invention, the sensing film, in a preferred embodiment of the present invention, is mechanically robust when the tensile and flexural strengths of the composite film are at least 90% of the tensile and flexural strengths of the neat polymer.

Tested fluids may typically be aqueous, and another preferred property of the present invention may include being impervious to water molecules, such as if the fluid is water-based or includes water vapor. Water vapor may interfere with the luminescence of the luminophore, creating inaccurate readings by the detector. Thus, the sensing film may preferably be hydrophobic to ensure that water molecules do not interfere with the luminophores in the sensing film. For purposes of the present invention, the sensing film, in a preferred embodiment of the present invention, is sufficiently hydrophobic when the contact angle of the distal face of the sensing film (i.e., the face of the sensing film that is exposed to the fluid under test), is greater than or equal to about 80°.

The sensing film of the present invention, therefore, may include one or more of the properties listed above. It has been found that a sensing film of the present invention maintains accurate oxygen sensing in a test fluid for a substantial period of time without significant degradation. The degree of photobleaching, for purposes of the present invention, is measured by comparing the quenching ratio (Q) at the start of the measurement cycle ("starting quenching ratio") and after a fixed number of oxygen concentration measurements using the sensing film. For purposes of the present invention, the sensing film of the present invention has substantially reduced photobleaching when the quenching ratio of the sensing film after 10,000 oxygen concentration measurements is greater than or equal to about 95% of the starting quenching ratio. Alternatively, the sensing film of the present invention has substantially reduced photobleaching when the quenching ratio of the sensing film after 20,000 oxygen concentration measurements is greater than or equal to about 95% of the starting quenching ratio. Alternatively, the sensing film of the present invention has substantially reduced photobleaching when the quenching ratio of the sensing film after 50,000 oxygen concentration measurements is greater than or equal to about 95% of the starting quenching ratio. Alternatively, the sensing film of the present invention has substantially reduced photobleaching when the quenching ratio of the sensing film after 10,000 oxygen concentration measurements is greater than or equal to about 97% of the starting quenching ratio. Alternatively, the sensing film of the present invention has substantially reduced photobleaching when the quenching ratio of the sensing film after 50,000 oxygen concentration measurements is greater than or equal to about 97% of the starting quenching ratio.

One non-limiting class of suitable polymer films is ultraviolet curable silicones, which includes without limitation acrylate- or methacrylate-functional polydimethylsiloxanes. Curable silicones are characterized by monomer units containing both siloxanes, an ultraviolet curable moiety such as an acrylate double bond, and includes a photoinitiator. Upon exposure to ultraviolet light in the presence of a photoinitiator, the double bonds of the ultraviolet curable moieties react with one another to crosslink and provide a cured resin. Advantages associated with the use of ultraviolet silicones as the polymer matrix include, the curing takes place quickly at relatively low temperatures, allowing the molybdenum clusters to remain as isolated monomers; being hydrophobic (for example, the water contact angle greater than about 90°); and eliminating the emission of harmful catalysts and/or reaction byproducts.

To make a sensing film, a solution of ultraviolet curable silicone monomers, photoinitiator, and molybdenum clusters/luminophores is spread as a film. Methods for spreading the solution include drop coating, spin coating, and spray coating. After the sensing film solution is applied to an appropriate thickness, it is then exposed to ultraviolet radiation, preferably in an inert atmosphere such as in a 100% pure nitrogen environment, to cure the polymer in situ with the cluster dispersed as isolated monomers within. It is believed that this in situ curing of the polymer matrix leads to advantageous properties of the sensing film.

Photocuring of ultraviolet curable silicones is a rapid process and the matrix is completely cured within a matter of minutes. By photocuring the silicone materials in the presence of the molybdenum clusters to achieve rapid crosslinking, the clusters are essentially "locked in" to a porous network. This locking-in is the preferred method for encapsulating the luminophore, as it believed to avoid deleterious matrix-cluster bonds that may hinder the clusters' performance. It further eliminates the need for modifying the cluster for grafting to the matrix, as this would complicate the cluster preparation. In addition, advantages are believed to flow from the fact that the photocured polymer retains its original volume so that the material does not suffer from any shrinkage.

As a result of the selection of materials and/or the method of locking-in thus described, it is believed that the photocured silicone is inert and immune to many common contaminants. Its robustness has been confirmed in field testing of the sensing film where it has been shown to give equally good results in environments with high acidity (pH of about 2), high basicity (pH of about 12), pure and diluted alcohol (e.g., methanol and ethanol), saturated ammonium chloride, sodium lauryl sulfate, and high concentrations of iron and calcium.

Another non-limiting class of suitable polymer films includes those produced from methacrylate polymers such as poly(butyl)methacrylate (PBMA) and poly(isobutyl) methacrylate (PIBMA). Copolymers such as poly(isobutyl methylacrylate-co-butyl methacrylate) can also be used. When these materials are employed, suitable solvents include butyronitrile. While the method of fabrication is different from that of the photocured silicone, the resulting film offers many of the same benefits as those previously described.

Another method for producing the sensing film is to apply a solution containing the luminophore directly to the end of the waveguide and then cure the solution in situ. This approach provides for a conformal coating of the waveguide and results in the smallest possible probe.

Luminophores-Molybdenum Clusters

A first class of luminophores found to give advantageous performance in the oxygen sensors described herein have general formula (1):

$$M_2Mo_nW_{6-n}X_{14} \tag{1}$$

wherein n is from 0 to 6, M is selected from K$^+$, Na$^+$, and NH$_4^+$, and each X is independently a monoanionic ligand. In preferred embodiments, n is greater than 0 and in one embodiment, n is equal to 6. The monoanionic ligand X is preferably a halide such as Cl$^-$, Br$^-$, F$^-$, or At$^-$. In preferred embodiments, the monoanionic ligand X is selected from Cl– and Br–. In certain embodiments, X is Cl$^-$. In general, the 14 X in the clusters can be the same or different. In a preferred embodiment, the X are all the same. Exemplary clusters include K$_2$Mo$_6$Cl$_{14}$, Na$_2$Mo$_6$Cl$_{14}$, and (NH$_4$)$_2$Mo$_6$Cl$_{14}$. Hydrates and solvates of the luminophores of general structure M$_2$Mo$_n$W$_{6-n}$X$_{14}$ can also be used. These luminophores are considered "salts" of the molybdenum cluster.

A second class of luminophores found to give advantageous performance in the oxygen sensors described herein have general formula (2):

$$Mo_nW_{6-n}X_{12} \tag{2}$$

wherein n is from 0 to 6, and each X is independently a monoanionic ligand. In preferred embodiments, n is greater than 0 and in one embodiment, n is equal to 6. The monoanionic ligand X is preferably a halide such as Cl$^-$, Br$^-$, I$^-$, F$^-$, or At$^-$. In preferred embodiments, the monoanionic ligand X is selected from Cl$^-$ and Br$^-$. In certain embodiments, X is Cl$^-$. In general, the 12 X in the clusters can be the same or different. In a preferred embodiment, the X are all the same. An exemplary cluster is Mo$_6$Cl$_{12}$. These luminophores are considered the "neutral" molybdenum cluster.

In those applications for which molybdenum clusters are the preferred luminophore, the salts of the molybdenum cluster may be advantageous for composite sensing films which require a high temperature cure for (i) densification or polymerization or (ii) driving off residual solvents following a photoinitiated densification or polymerization. If the matrix densification process does not require a high temperature cure, the neutral clusters may be advantageous.

The ground state of the oxygen molecule is a spin triplet, the excited state is a spin singlet. Chemical and biological applications require monitoring both triplet and singlet oxygen. Following photoexcitation, the long lived phosphorescence from the molybdenum chloride clusters is quenched by ground state triplet oxygen. In one embodiment, measurements of the phosphorescent emission from of the molybdenum chloride clusters are used for sensing ground state triplet oxygen. In another embodiment, time resolved measurements that separate the long and short components of the luminescence from the molybdenum clusters can be used to sense excited state singlet oxygen. In another embodiment, other suitable luminophores can be used for sensing excited state singlet oxygen The present invention allows for the use of a luminophore for detecting triplet oxygen, a luminophore for detecting singlet oxygen, or the use of multiple luminophores for simultaneously detecting both triplet and singlet oxygen.

Light Blocking Layer

Since the sensor described herein in an optical sensor, performance is typically improved by blocking environmental light from entering the sensing system. The light blocking layer may preferably block all wavelengths of light from entering the sensing system. Alternatively, the light blocking layer may block only the wavelengths that may excite the luminophore and/or luminesce from the luminophore, thereby providing a more accurate excitation and detection thereof. In an exemplary example, this may be accomplished by covering the sensing film 14 with a film containing light blocking pigments 66 such as carbon black. With the use of the light blocking layer, the signal to noise ratio of the sensor can be improved because the only light reaching the detector 12 is from the luminescence emitted by the clusters in the sensing film 14. Spurious optical signals in the UV wavelength range, for example from external sources such as sunlight or room lights, are eliminated by the light blocking layer. The thickness of the light blocking layer is optimized for the specific application; thicker layers will typically result in better signal to noise ratios but may slow down the sensor response time.

In another embodiment, the light blocking film may additionally be hydrophobic, thereby preventing water molecules from contacting the sensing film.

There are numerous manners in which the functionality of the light blocking layer can be provided, including the use of a separate layer which is assembled along with the other components of the sensing film assembly, the direct incorporation of light blocking materials into the sensing film directly, and the application of a conformable layer to the sensing film, applied, for example, in a spray-on manner.

Mode of Operation

In a non-limiting manner, the sensor detects oxygen in the following manner. The outer layer of the sensor, typically the light blocking layer 66, is exposed to the fluid in which oxygen is to be detected or measured. Oxygen in the fluid is present in the sensing film by equilibrium. When the molybdenum clusters in the sensing film 14 are excited by the incoming photons 18, the clusters are put into an excited state. The clusters return to the ground state by emission of photons 20, which in certain embodiments have a peak wavelength of about 750 nm. The properties of this luminescence are dependent on the oxygen concentration in the fluid, and thereby the sensing film 14, and is well described by the Stern-Volmer relationship.

The Stern-Volmer relationship is given by $$\tau_0/\tau = 1 + K_{sv}[O_2]$$

wherein $\tau$ is the lifetime of the luminescence in the presence of oxygen, $K_{sv}$ is the Stern-Volmer constant, $[O_2]$ is the concentration of oxygen in the fluid, and $\tau_0$ is as defined above. Advantageously, luminescence by the molybdenum clusters in the sensing film as described herein shows a good fit to the Stern-Volmer plot, being linear with an intercept of 1. This allows a straight forward two point calibration of the sensor.

The Stern-Volmer relationship holds that the emission lifetime $\tau$ and the emission intensity of the luminescence of the molybdenum clusters is a function of the oxygen concentration in the fluid being measured. Since both parameters follow the same dependency on oxygen concentration, quenching of luminescence by oxygen can be monitored by measuring either parameter. In certain embodiments, it is advantageous to measure the emission lifetime instead of the intensity because the value of the emission lifetime does not directly depend on fluctuations in intensity of the light source, stray external light, and fluctuations in the detector sensitivity as do intensity measurements. The emission lifetime can be measured via two techniques, directly using photon counting techniques or indirectly via phase fluorimetry. From an instrumentation perspective it is possible to build a more robust and compact measurement system with higher signal to noise ratio, by using phase fluorimetry to monitor the emission lifetime instead of the emission intensity.

From measurements of the intensity or the emission lifetime on a series of standard oxygen mixtures, a calibration curve can be readily be obtained. It is understood that values relating to the percentage of oxygen in the fluid can be derived from the calibration curve. As a result the oxygenation level in the media is known from the measured emission lifetime or the measured intensities.

The molybdenum based, purely inorganic luminophore has advantageous optical properties when used in the sensors described herein. Those advantages include a long lifetime of luminescence, a large Stokes shift, a resistance to photobleaching, and a linear Stern-Volmer plot with an intercept of 1. Although the invention is not limited to theory, it is believed that the suitability of the particular molybdenum clusters described herein is at least in part due to its lack of conjugated or organic structure which minimizes matrix effects. An advantageous behavior of a hydrophobic sensing film protects the luminophore molybdenum clusters from irreversible fouling by water. The clusters in the matrix are characterized by desirable levels of thermal and photochemical stability.

Figure 5:
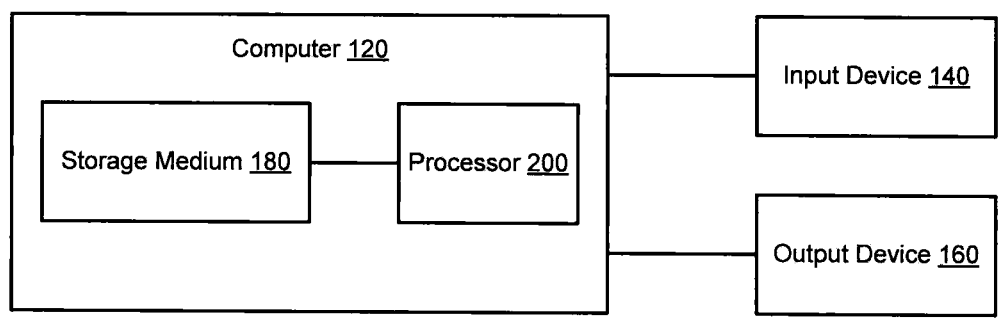
FIG. 5 shows a diagram of a computer that can be used to implement certain aspects of embodiments of the invention.

In various embodiments, the present invention may include one or more computers and may additionally be connected to one or more computers, see FIG. 5. For example, the electronics module 32 may take the form of a microcontroller, a special class of computers used for embedded application. In those embodiments in which more than one computer is used, the computers may be in operative communication with one another through a variety of wired or wireless mechanisms, or through physical transfer of computer-readable media among the computers. The computers may be in communication via a local-area network (LAN) and/or via the Internet or other large-scale computer network. As shown in FIG. 5, each computer 120 may have an input device 140, an output device 160, a storage medium 180, and a processor 200. Possible input devices 140 include a keyboard, a computer mouse, a touch screen, the electronics module 32, and the like. Output devices 160 include a display device, printer, control valves, alarms, and the like. Storage media 180 include various types of memory such as a hard disk, RAM, flash memory, and other magnetic, optical, physical, or electronic memory devices, whether fixed or removable. The processor 200 is any computer processor capable of performing calculations and directing other functions for performing input, output, calculation, and display of data in the disclosed invention. In various embodiments, one or more steps of the claimed methods may be executed using the processor 200. In various embodiments, the invention may include a computer program product including a computer usable medium (e.g. storage media 180 as described above) having a computer readable program code embodied thereon, where the computer readable program code is adapted to be executed (e.g. using a processor 200) to implement methods of the invention.

The one or more computers which may be present can be used to perform a number of useful tasks. Non-limiting examples include: 1) modifying sensing parameters to allow the same physical sensor to be used in liquids, wet gases, and dry gases; 2) providing oxygen level information to a human supervisor and/or alerting said supervisor should oxygen levels move outside a prescribed range; and 3) controlling an industrial process, with the measured oxygen level serving as part of a closed-loop feedback system.

EXAMPLES

The following examples illustrate the preparation of an exemplary sensing film, primer, substrate, and light blocking layer; and presents experimental data obtained from an exemplary sensor comprising said components.

Exemplary Sensing Film Preparation

Molybdenum clusters are dispersed into an acrylated silicone resin (Gelest UMS-182; approximate molecular weight 5567; 15-20% acrylated). The presence of acrylate functional groups allows for a free radical cure, in this case photo-initiated cure using benzoin ethyl ether (BEE) as a photo-catalyst. The 254 nm line from a mercury lamp activates the BEE in an oxygen free environment. This combination was chosen as it lies outside the absorption window of the cluster. The clusters were dissolved into a mixture of acetone and acetonitrile. The acetonitrile solvates the clusters to ensure good sensor performance while the acetone acts as an emulsifier between the non-polar silicone and polar acetonitrile. A centrifugal shear mixer was used to blend the components.

An exemplary sensing film was prepared by following this procedure.

1. 75 mg of clusters of $K_2Mo_6Cl_{14}$ were dissolved into a mixture of 2 g acetonitrile and 8 g acetone (5.3 mM) in a 20 ml glass scintillation vial. The vial was wrapped in aluminum foil to shield the solution from light and the solution was continually stirred until the clusters had dissolved. The cluster solution was stored in the dark until needed.
2. In a 10 g capacity shear mixing cup (heretofore referred to as a "vessel"), 1.0 g of the cluster solution from step 1 was added to 2.5 g of [15-20% (acryloxypropyl)methylsiloxane]-dimethylsiloxane copolymer (UMS-182).
3. The vessel from step 2 was capped tightly and mixed in a high shear centrifugal mixer at 3000 RPM for 3 minutes. Alternatively the vessel from step 2 may be capped tightly and mixed in a low shear centrifugal mixer for an extended period.
4. After removal from the shear mixer, 0.113 ml of 0.3M benzoin ethyl ether in acetone was added to the UMS-182/cluster mixture. This produces an initiator to resin ratio of 1:20.
5. Solution from step 4 was then recapped and mixed again in the high shear centrifugal mixer at 3000 RPM of 3 minutes. Alternatively, solution from step 4 may be mixed in a low shear centrifugal mixer for an extended period.
6. A freshly primed slide (see Primer Selection and Preparation of Primed Slides) was placed into a lamp housing. The lamp housing consists of a mercury lamp and a reflector that allows for treatment of both sides of the sample at once. Uneven treatment may result in internal stresses due to uneven curing and may result in sample cracking. The lamp housing is located in a gas tight box that allows for purging.
7. On the order of 5-15 µl of solution from step 5, depending on the desired thickness, were added to the primed slide.
8. The slide was purged under flowing nitrogen (or noble gas) to remove oxygen. The mercury lamp was turned on and the slide was exposed to the ultraviolet light for 5-15 minutes.
9. The slide was post-treated by placing it under vacuum for 24 h to remove any residual solvent.

Several variables were examined when developing the sensing film chemistry. The effect of cluster concentration on sensor performance was evaluated by changing the cluster solution concentration in the sensing film preparation. In addition to the 5.3 mM cluster solution, 0.88 mM, 1.7 mM, and 2.7 mM were also prepared, coated onto quartz slides. These slides were tested in gaseous $N_2$ and $O_2$. The results presented in Table 1 include (i) the unquenched lifetime $\tau_0$, (ii) the lifetime in 21% oxygen $\tau_{21}$, and (iii) the quenching ratio Q. A larger value for Q is desirable, which indicates that the higher cluster loading (5.3 mM) is the best of those ratios examined. The resin to initiator ratio in each material was 20:1.

TABLE 1

| Cluster Solution Concentration (mM) | Weight % | $\tau_0$ | $\tau_{21}$ | Q |
|---|---|---|---|---|
| 0.88 | 0.5 | 55 | 38 | 1.5 |
| 1.7 | 1.0 | 67 | 36 | 1.9 |
| 2.7 | 1.5 | 77 | 20 | 3.9 |
| 5.3 | 3.0 | 123 | 23 | 5.4 |

The effect of the resin to initiator ratio on sensor performance was evaluated. Initially, solid initiator was added directly to the resin mixture, but for convenience the initiator was dissolved in acetone (0.3M) and an accurate volume was pipetted into the resin/cluster mixture. Initiator to resin ratios of 1:5, 1:10, 1:20, and 1:40 were prepared, coated onto quartz slides. Again the slides were tested in gaseous $N_2$ and $O_2$. The results, presented in Table 2, indicate that the sensor performance improves with initiator dilution, with a maximum in the range in the 1:20-1:40.

TABLE 2

| Initiator to Resin ratio | $\tau_0$ | $\tau_{21}$ | Q |
|---|---|---|---|
| 1:5 | 98 | 42 | 2.3 |
| 1:10 | 90 | 25 | 3.6 |
| 1:20 | 123 | 23 | 5.4 |
| 1:40 | 122 | 23 | 5.4 |

Primer Selection and Preparation of Primed Slides

The sensing film may preferably be deposited onto transparent surfaces, such as slides and optical fibers; or onto release materials, which can be removed to form free standing films. Materials such as glass (or quartz), plastics (PMMA), or silicones can all act as substrates provided they meet the aforementioned requirements for substrates. Note that the film preparation can be done by either spin coating or spraying coating in an appropriate enclosure, as well as drop coating.

In one embodiment, the sensing film 14 was produced from photo-cured silicone, which is a non-polar (low surface energy) material with a very high coefficient of thermal expansion (~600 ppm/° C.). Both of these properties create problems with adhesion to quartz, a polar surface (high surface energy) material with a low coefficient of thermal expansion (1 ppm/° C.). The incompatibility of the surfaces leads to a weak interface. In addition, even mild temperature variations can lead to significant thermal induced stress at the interface, leading to spontaneous delamination. To alleviate the adhesion issues, a primer was placed between the quartz substrate and sensing film to act as an adhesion promoter. The primer material used was a film of methacryloxymethyltriethoxysilane that adheres to the quartz via silane-silica interaction and adheres to the sensing film via crosslinking through the methacrylic functional group.

The quartz substrates were primed by the following procedure.

1. Quartz slides with one side frosted were first cleaned by sonication in ethanol followed by acid and then thoroughly rinsed with deionized water.
2. A solution of the primer, methacryloxymethyltriethoxysilane, which was used neat was prepared; alternatively, a solution may be prepared by diluting the primer with methyl alcohol in a 1:2 or 1:3 ratio.
3. The film was applied to the frosted side quartz substrate using a spin coater at 6000 RPM for 60 seconds.
4. The primed slides were then heated to 120° C. under ambient conditions, followed by vacuum pumping. Primed slides are kept at high temperature until the application of the sensing film.

The primer layer produced was as thin as possible, as excess primer may diffuse into sensing film and hinder sensor performance. It has also been determined that the primed slides, produced using the method outlined, do not have a long shelf life and that the sensing film must be applied as soon as possible. However, those skilled in the art could devise alternative formulations with an extended shelf life.

For the embodiments in which the substrate is retained as part of the sensing probe, a frosted glass slide is preferred because the increased surface area, as compared to a smooth slide, promotes adhesion of the sensing film. The frosting is additionally believed to improve sensor performance by preferentially scattering the excitation photons throughout the sensing file, thereby increasing the luminescence; and by preferentially scattering the emitted photons back to the detector, thereby increasing the detector signal.

Light Blocking Layer

The light blocking layer was prepared as a film by first mixing two part clear RTV (Silicone) with 5-10% carbon black (CB) in a shear mixer. The product was thinned with hexane and sprayed onto a thin Teflon sheet to form a thin CB-RTV layer. The Teflon sheet simply provides a platform to form a free-standing CB-RTV film. After curing the film at 150° C., the light blocking layer is ready to be used as a top protective coat or alternatively may be used as a substrate For use as a top protective coat, the prepared CB-RTV film was placed over a sensing film which was formed on a substrate, or alternatively, may have been formed directly onto the sensing film.

For use as a substrate, a sensing film was prepared by applying a 5-50 µL of the cluster solution onto a 7 mm-70 mm diameter CB-RTV substrate in a closed vessel to form a thin film. The thickness of film is controlled by amount of cluster solution on the substrates. The vessel was purged with an inert gas (nitrogen) to remove oxygen and the film was irradiated by ultraviolet light (254 nm) from the top. The film was completely cured within a couple of minutes, but to ensure the complete curing, it may be left for longer time.

Performance Data for the Oxygen Sensor

A number of experiments were performed using several embodiments of the presently described invention. FIGS. 6-9 show representative measurements of dissolved oxygen in water based on these experiments. For the experiments, the sensors were fabricated using the techniques described in the preceding examples; the light blocking layer was in direct contact with the water; and an off-the-shelf compact phase sensitive fluorimeter was used as the detector for luminesced photons 12.

Figure 6:
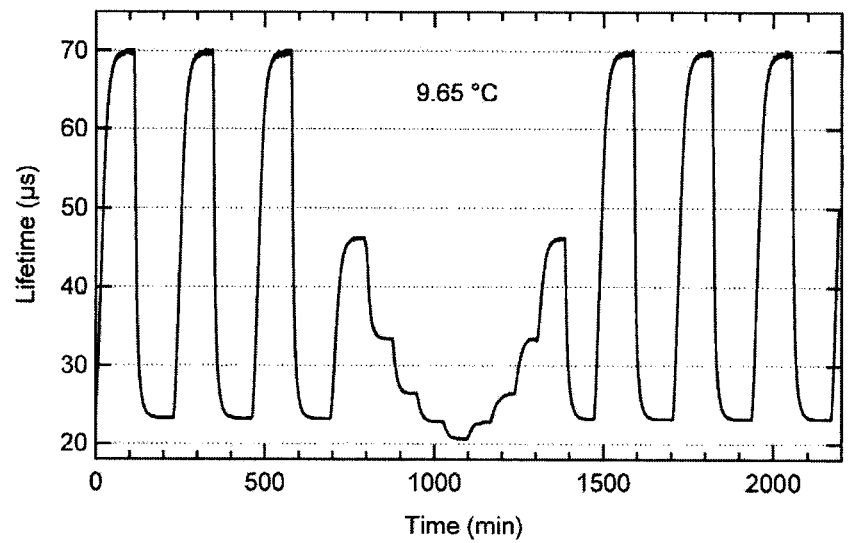
FIG. 6 shows a plot of optical oxygen sensor signal lifetime in 10° C. water as a function of time over a 2190 minute period.
Figure 7:
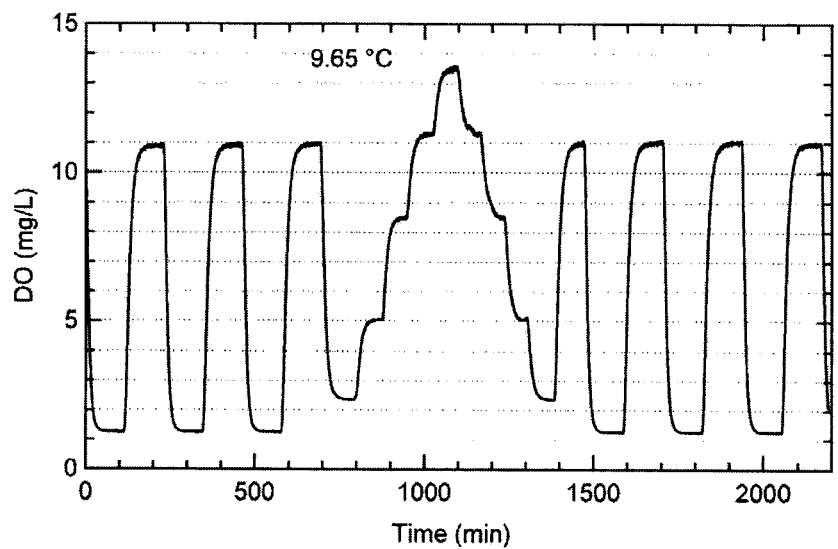
FIG. 7 shows a plot of oxygen concentration as calculated from the output from the optical oxygen sensor system in 10° C. water as a function of time over a 2190 minute period.

FIGS. 6 and 7 show continuous sensor measurements over a 2190 minute period (one data point per 10 s). The water temperature was maintained at 9.65° C. In order to ascertain the sensor stability, the sensor response at the two extremes of oxygen concentration, the absence of oxygen (99.999% $N_2$) and laboratory air (20.9% $O_2$), were measured for three complete cycles at both the beginning and end of the 2190 minutes experiment. As given in Table 3, in the absence of oxygen and oxygen saturated water, the signal/noise ratio is better than 150 and with an uncertainty in the measurement less than 3.5%.

TABLE 3

| | number of measurements | lifetime (µs) | signal/noise |
|---|---|---|---|
| $N_2$ (<0.001% $O_2$) | 6 | 69.74 ± 0.10 | 175 |
| lab air (20.9% $O_2$) | 6 | 23.21 ± 0.08 | 150 |

A complete calibration curve was obtained between 700 and 1400 min by sequentially bubbling oxygen mixtures of 4.44%, 10.00%, 16.15%, 21.50%, 26.07%, 21.50%, 16.15%, 10.00% and 4.44% (balance is $N_2$). The dissolved oxygen concentration in the water bath was calculated using Henry's Law coefficients. The raw lifetime data of FIG. 6 converted to dissolved oxygen in units of mg/L is shown in FIG. 7.

Figure 8:
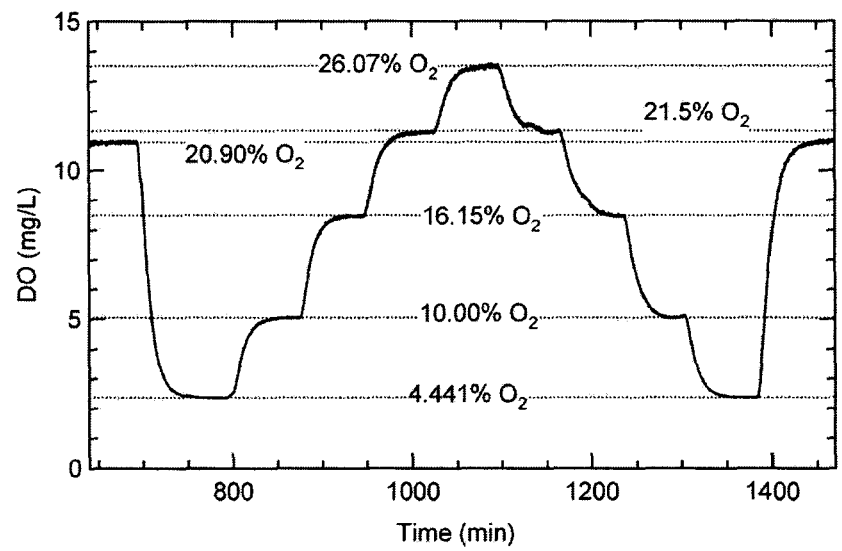
FIG. 8 shows a detailed plot of oxygen concentration as calculated from the output from the optical oxygen sensor system in 10° C. water over an 825 minute period.

FIG. 8 shows an expanded view of the data from 640 to 1465 minutes. As a guide to the eye, the signal levels at 4.44%, 10.00%, 16.15%, 20.90%, 21.50% and 26.07% are indicated. Flat reproducible steps are observed at each oxygen level with minimum hysteresis while increasing or decreasing oxygen concentration. There is no evidence of photobleaching over the 13,000 data points. The data demonstrate the sensitivity, reversibility and high signal/noise ratio of the sensor for real-time continuous monitoring of oxygen.

Figure 9:
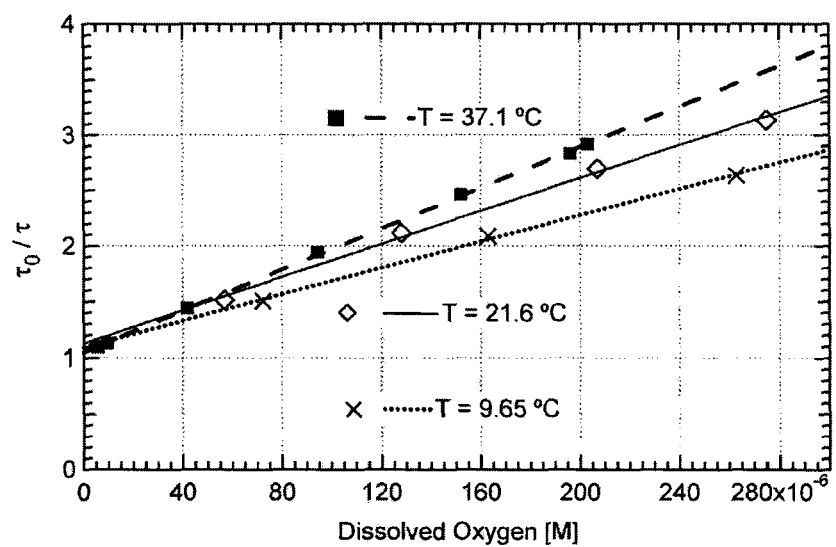
FIG. 9 shows a plot of optical oxygen sensor film performance in water at 9.6, 22 and 37° C. as a function of molar oxygen concentration.

A second experiment with the same sensor, shown in FIG. 9 demonstrates the optical sensor performance in water over the temperature range of 9.65 to 37.1° C. Plotted is the sensor response, measured in term of the lifetime ratio $\tau_0/\tau$, at 9.65, 21.6 and 37.1° C. as a function of molar dissolved oxygen concentration. The data were fit to the Stern-Volmer equation:

$$\tau_0/\tau = 1 + k_q \tau_0 [O_2],$$

where $\tau$ is the lifetime in the presence of oxygen, $k_q$ is the molar rate constant, $[O_2]$ the molar oxygen concentration, and $\tau_0$ is as defined above. Note that the data point for $[O_2]=0$ is not included in the fit. The table lists both the fit parameters to the Stern Volmer equation along with the photophysical parameter, $\tau_0$ and $k_q$ which are obtained from the fit.

TABLE 4

| Temperature (C.) | $\tau_0$ (μs) | a# | b (M$^{-1}$)# | $k_q$ (M$^{-1}$ s$^{-1}$) |
| --- | --- | --- | --- | --- |
| 9.65 | 69.7 | 1.09 ± 0.05 | 5900 ± 250 | 8.5 × 10$^7$ |
| 21.6 | 65.4 | 1.13 ± 0.06 | 7400 ± 300 | 11.4 × 10$^7$ |
| 37.1 | 46.0 | 1.05 ± 0.01 | 9195 ± 85 | 20.0 × 10$^7$ | linear fit parameter to $\tau_0/\tau = a + b$ [M]

For the entire temperature range a linear fit with an intercept of 1.0 is obtained, which indicates (i) that the bi-molecular quenching processes is dominated by a single lifetime; (ii) the optical indicator is well dispersed in the polymer sensing film, and (iii) cluster to cluster interactions as well as indicator/matrix interactions have been minimized within the sensing film. The superior properties of the sensing material for monitoring oxygen over a range of industrial and biologically relevant temperatures are demonstrated by this data.

From our data we conclude:
1. the sensing film is permeable to oxygen;
2. there is no evidence of photobleaching from 2190 minutes of measurement which encompasses 13,000 data points;
3. the optical indicator is well dispersed in the polymer matrix with minimum cluster/matrix interactions;
4. immobilization of the cluster in the polymer matrix does not affect the unique photophysical properties of the MoCl cluster;
5. poisoning by water is not a problem;
6. the sensing film is stable over extended periods, with excellent repeatability, very little drift and minimum hysteresis; and
7. the quenching ratio after 13,000 measurements is 99.8% of the quenching ratio at the beginning of the data set.

Performance of the $K_2Mo_6Cl_{14}$ Luminophore Immobilized in the Composite Polymer Matrix It is well known by one skilled in the art that immobilization of a luminophore in a matrix leads to significant degradation of the optical properties of the luminophore when compared to the isolated luminophore in its preferred solvent. In order to ascertain the optical quality of the $K_2Mo_6Cl_{14}$/polymer composite sensing film, as reported in Table 4, the optical properties of the isolated luminophore itself were measured. The parameters of interest are the $\tau_0$ (solution) and a quenching ratio Q*, which is $\tau_0$ (solution) divided by $\tau_{21}$ (solution). Using Stern-Volmer analysis on lifetime measurements of a 70 μM solution of $K_2Mo_6Cl_{14}$ in $CH_3CN$ at 22 C, we obtained $\tau_0$ (solution)=160 μs and Q*=14. These numbers for a well dispersed cluster in its preferred solvent represent the theoretical upper bound for the cluster immobilized in any matrix. From Table 3 at 22 C for the $K_2Mo_6Cl_{14}$/polymer composite sensing film we obtain $\tau_0$ (composite)=65 μs and Q=3 for measurements of dissolved oxygen in water. One skilled in the art would anticipate: 1) that $\tau_0$ (composite) would be at least a factor of 10 less than $\tau_0$ (solution), whereas using the method presently disclosed, we observe a decrease of only a factor of 2.5; and 2) that Q would be at least as factor of 10 less than Q*, whereas using the method presently disclosed, we observe a decrease of only a factor of 5. This marked improvement leads to an oxygen sensing film that is extremely sensitive to oxygen in water (signal/noise ratio>150) over the entire range of oxygen concentration (0% to 21%).

A second comparison of the optical performance of the $K_2Mo_6Cl_{14}$/polymer composite sensing film given in Table 4, is given with respect to published data for a $Mo_6Cl_{12}$-derivatized poly(4-vinylpyridine) polymer [J A Jackson, M D Newsham, C Worsham, D G Nocera. Chem. Mater., 8(2):558-564 (1996)] From measurements in room temperature water the authors report an oxygen quenching constant $k_q \sim 18 \times 10^5$ [M]$^{-1}$ s$^{-1}$. For the sensing film described above, we obtain $k_q = 11 \times 10^7$ [M]$^{-1}$ s$^{-1}$; therefore the composite film composed of $K_2Mo_6Cl_{14}$ luminophores immobilized in a photo-cured silicone polymer, is superior by about 2 orders of magnitude.

While certain representative embodiments and details have been shown for purposes of illustrating the invention, it will be apparent to those skilled in the art that various changes may be made without departing from the scope of the disclosure, which is further described in the following appended claims.

We claim:
1. A composite comprising:
at least one polymer and an amount of at least one luminophore,
the composite formed by dispersing the luminophore as isolated clusters within a solution comprising a solvent wherein the luminophore within the solution has an unquenched emission lifetime $\tau_0$ (solution) that is linear, blending an amount of photocurable silicone monomers into the solution, and rapidly photocuring with ultraviolet light the ultraviolet curable silicone monomers with the amount of at least one luminophore dispersed therein as isolated clusters to form a polymer matrix wherein the polymer is crosslinked and the luminophore is dispersed as isolated clusters within the polymer matrix,
wherein the luminophore comprises a hexanuclear molybdenum compound selected from the group consisting of those of formula (1) and those of formula (2):

$$M_2Mo_nW_{6-n}X_{14} \qquad (1)$$

$$Mo_nW_{6-n}X_{12} \qquad (2)$$

wherein M is a cation selected from the group consisting of Na$^+$, K$^+$ and NH4$^+$, wherein n is 0 to 6, and wherein each X is independently a monoanionic ligand,
wherein the composite has the following property indicating that the luminophore is dispersed as isolated clusters within the polymer matrix: an ending quenching ratio of about 95% or more of a starting quenching ratio in a measurement cycle wherein in the measurement cycle the composite is photoexcited 10,000 times, each photoexcitation for a duration and with energy at least sufficient to excite the luminophore from the ground state to the excited state, wherein the starting quenching ratio is measured at the start of the measurement cycle and the ending quenching ratio is measured at the end of the measurement cycle.

2. The composite of claim 1, wherein the composite is a film.

3. The composite of claim 1 wherein the X are selected from the group consisting of Cl⁻, Br⁻, F⁻, I⁻ and At⁻.

4. The composite of claim 1, wherein the luminophore is selected from the group consisting of $K_2Mo_6Cl_{14}$, $Na_2Mo_6Cl_{14}$, $(NH_4)_2Mo_6Cl_{14}$, $Mo_6Cl_{12}$, and blends thereof.

5. The composite of claim 1, wherein the polymer matrix comprises a photocured polymer selected from the group consisting of acrylate-functional polydimethylsiloxanes, methacrylate-functional polydimethylsiloxanes, acrylate- and methacrylate-functional polydimethylsiloxanes, and blends thereof.

6. An oxygen sensor, comprising:
a sensing film formed from the composite of claim 1;
a source of excitation photons having a first wavelength;
an optical waveguide directing the source of excitation photons to the sensing film wherein the excitation photons excite the luminophores within the sensing film causing the luminophores to emit luminesced photons of a second wavelength; and
a detector for detecting the luminesced photons from the sensing film configured to measure the amount of oxygen in a fluid based on the detected luminesced photons.

7. The oxygen sensor of claim 6, further comprising:
a second optical waveguide wherein the detector is connected to the second optical waveguide and further wherein the second optical waveguide is connected to the sensing film, and further wherein the second optical waveguide directs the luminesced photons from the sensing film to the detector.

8. The oxygen sensor of claim 6 further comprising:
an index matching material disposed in a location selected from the group consisting of: between the sensing film and the optical waveguide, between the source of excitation photons and the optical waveguide, and between the detector and the optical waveguide.

9. The oxygen sensor of claim 6 wherein the optical waveguide comprises a fiber optic cable.

10. The oxygen sensor of claim 6 wherein the optical waveguide comprises a bundle of optical waveguide elements.

11. The oxygen sensor of claim 6 further comprising:
a substrate wherein the sensing film is disposed on and supported by the substrate.

12. The oxygen sensor of claim 11 further comprising:
a primer between the substrate and the sensing film to promote adhesion of the sensing film to the substrate.

13. The oxygen sensor of claim 6 further comprising:
a light blocking layer covering the sensing film and operatively connected to the sensing film to block interfering wavelengths of light from entering the oxygen sensor.

14. The oxygen sensor of claim 6 further comprising:
a computer for processing data collected by the detector, wherein the computer performs a task based on the data collected by the detector.

15. A composition comprising a photocured silicone polymer and molybdenum clusters, wherein the molybdenum clusters comprise hexanuclear molybdenum compounds selected from the group consisting of those of formula (1) and those of formula (2):

(1)

(2)

wherein M is a cation selected from the group consisting of Na⁺, K⁺ and NH₄⁺, wherein n is 0 to 6, and wherein each X is independently a monoanionic ligand,
wherein the composition is a film formed by dissolving the molybdenum clusters in a solvent to form a solution wherein the molybdenum clusters are dispersed within the solution as isolated clusters and the solution has an unquenched emission lifetime $\tau_0$ (solution) that is linear, blending the solution with ultraviolet curable silicone monomers to form a mixture, and, and photocuring the mixture with ultraviolet light to rapidly crosslink the ultraviolet curable silicone monomers to form the photocured silicone polymer having the molybdenum clusters dispersed therein as isolated clusters.

16. The composition of claim 15 wherein the solvent is selected from the group consisting of acetone, acetonitrile and blends of acetone and acetonitrile.

17. A composite comprising:
at least one polymer selected from the group consisting of an ultraviolet cured silicone polymer forming a polymer matrix; and an amount of at least one luminophore dispersed within the polymer matrix, the composite formed by dispersing the luminophore as isolated clusters within a solution comprising a solvent wherein the luminophore within the solution has an unquenched emission lifetime $\tau_0$ (solution) that is linear, blending an amount of photocurable silicone monomers into the solution, and rapidly photocuring the monomers with the amount of at least one luminophore to form a polymer matrix wherein the polymer is crosslinked and the luminophore is dispersed as isolated clusters within the polymer matrix,
wherein the luminophore comprises a hexanuclear molybdenum compound selected from the group consisting of those of formula (1) and those of formula (2):

(3)

(4)

wherein M is a cation selected from the group consisting of Na⁺, K⁺ and NH₄⁺, wherein n is 0 to 6, and wherein each X is independently a monoanionic ligand,
wherein the composite has the following properties, wherein the following properties indicate that the luminophore is dispersed as isolated clusters within the polymer matrix:
$\tau_0$ (solution)/$\tau_0$ (composite) is less than or equal to 3.5, where $\tau_0$(composite) is the unquenched emission lifetime of the composite in a fluid; and
a quenching ratio of the luminophore within the composite is greater than or equal to 2.5.

18. The composite of claim 17, wherein the composite is a film.

19. The composite of claim 17 wherein the X are selected from the group consisting of Cl⁻, Br⁻, F⁻, I⁻ and At⁻.

20. The composite of claim 17, wherein the luminophore is selected from the group consisting of $K_2Mo_6Cl_{14}$, $Na_2Mo_6Cl_{14}$, $(NH_4)_2Mo_6Cl_{14}$, $Mo_6Cl_{12}$, and blends thereof.

21. The composite of claim 17, wherein the polymer matrix comprises a photocured polymer selected from the group consisting of acrylate-functional polydimethylsiloxanes, methacrylate-functional polydimethylsiloxanes, acrylate- and methacrylate-functional polydimethylsiloxanes, and blends thereof.

22. An oxygen sensor, comprising:
a sensing film formed from the composite of claim 17;
a source of excitation photons having a first wavelength;

an optical waveguide directing the source of excitation photons to the sensing film wherein the excitation photons excite the luminophores within the sensing film causing the luminophores to emit luminesced photons of a second wavelength; and a detector for detecting the luminesced photons from the sensing film configured to measure the amount of oxygen in a fluid based on the detected luminesced photons.

23. The oxygen sensor of claim 22, further comprising:

a second optical waveguide wherein the detector is connected to the second optical waveguide and further wherein the second optical waveguide is connected to the sensing film, and further wherein the second optical waveguide directs the luminesced photons from the sensing film to the detector.

24. The oxygen sensor of claim 22 further comprising:

an index matching material disposed in a location selected from the group consisting of: between the sensing film and the optical waveguide, between the source of excitation photons and the optical waveguide, and between the detector and the optical waveguide.

25. The oxygen sensor of claim 22 wherein the optical waveguide comprises a fiber optic cable.

26. The oxygen sensor of claim 22 wherein the optical waveguide comprises a bundle of optical waveguide elements.

27. The oxygen sensor of claim 22 further comprising:

a substrate wherein the sensing film is disposed on and supported by the substrate.

28. The oxygen sensor of claim 27 further comprising:

a primer between the substrate and the sensing film to promote adhesion of the sensing film to the substrate.

29. The oxygen sensor of claim 22 further comprising:

a light blocking layer covering the sensing film and operatively connected to the sensing film to block interfering wavelengths of light from entering the oxygen sensor.

30. The oxygen sensor of claim 22 further comprising:

a computer for processing data collected by the detector, wherein the computer performs a task based on the data collected by the detector.

31. The composite of claim 15 wherein the X are selected from the group consisting of $Cl^-$, $Br^-$, $F^-$, $I^-$ and $At^-$.

32. The composite of claim 15, wherein the molybdenum clusters are selected from the group consisting of $K_2Mo_6Cl_{14}$, $Na_2Mo_6Cl_{14}$, $(NH_4)_2Mo_6Cl_{14}$, $Mo_6Cl_{12}$, and blends thereof.

33. The composite of claim 15, wherein the polymer matrix comprises a photocured polymer selected from the group consisting of acrylate-functional polydimethylsiloxanes, methacrylate-functional polydimethylsiloxanes, acrylate- and methacrylate-functional polydimethylsiloxanes, and blends thereof.

34. An oxygen sensor, comprising:

a sensing film formed from the composite of claim 15;

a source of excitation photons having a first wavelength;

an optical waveguide directing the source of excitation photons to the sensing film wherein the excitation photons excite the luminophores within the sensing film causing the molybdenum clusters to emit luminesced photons of a second wavelength; and a detector for detecting the luminesced photons from the sensing film configured to measure the amount of oxygen in a fluid based on the detected luminesced photons.

35. The oxygen sensor of claim 34, further comprising:

a second optical waveguide wherein the detector is connected to the second optical waveguide and further wherein the second optical waveguide is connected to the sensing film, and further wherein the second optical waveguide directs the luminesced photons from the sensing film to the detector.

36. The oxygen sensor of claim 34 further comprising:

an index matching material disposed in a location selected from the group consisting of: between the sensing film and the optical waveguide, between the source of excitation photons and the optical waveguide, and between the detector and the optical waveguide.

37. The oxygen sensor of claim 34 wherein the optical waveguide comprises a fiber optic cable.

38. The oxygen sensor of claim 34 wherein the optical waveguide comprises a bundle of optical waveguide elements.

39. The oxygen sensor of claim 34 further comprising:

a substrate wherein the sensing film is disposed on and supported by the substrate.

40. The oxygen sensor of claim 39 further comprising:

a primer between the substrate and the sensing film to promote adhesion of the sensing film to the substrate.

41. The oxygen sensor of claim 34 further comprising:

a light blocking layer covering the sensing film and operatively connected to the sensing film to block interfering wavelengths of light from entering the oxygen sensor.

42. The oxygen sensor of claim 34 further comprising:

a computer for processing data collected by the detector, wherein the computer performs a task based on the data collected by the detector.

\* \* \* \* \*